United States Patent
Drmanovic

(10) Patent No.: US 10,391,294 B2
(45) Date of Patent: Aug. 27, 2019

(54) DISINFECTING CAP

(71) Applicant: Zoran Drmanovic, Palm City, FL (US)

(72) Inventor: Zoran Drmanovic, Palm City, FL (US)

(73) Assignee: DRMA GROUP INTERNATIONAL LLC, Palm City, FL (US)

(*) Notice: Subject to any disclaimer, the term of this patent is extended or adjusted under 35 U.S.C. 154(b) by 0 days.

(21) Appl. No.: 15/262,373

(22) Filed: Sep. 12, 2016

(65) Prior Publication Data

US 2018/0071508 A1    Mar. 15, 2018

(51) Int. Cl.
*A61M 39/16* (2006.01)
*A61M 39/20* (2006.01)
*A61M 39/18* (2006.01)

(52) U.S. Cl.
CPC ........ *A61M 39/162* (2013.01); *A61M 39/165* (2013.01); *A61M 39/18* (2013.01); *A61M 39/20* (2013.01)

(58) Field of Classification Search
CPC .. A61M 39/162; A61M 39/165; A61M 39/18; A61M 39/20
See application file for complete search history.

(56) References Cited

U.S. PATENT DOCUMENTS

| | | | |
|---|---|---|---|
| 2,400,722 A | 5/1946 | Swan | |
| 4,340,052 A | 7/1982 | Dennehey et al. | |
| 4,440,207 A * | 4/1984 | Genatempo | A61L 31/16 150/154 |
| 5,053,003 A | 10/1991 | Dadson et al. | |
| 5,242,425 A | 9/1993 | White et al. | |
| 5,295,975 A | 3/1994 | Lockwood, Jr. | |
| 5,324,264 A | 6/1994 | Whitaker | |
| 5,413,561 A * | 5/1995 | Fischell | A61M 39/0606 604/167.01 |
| 5,429,612 A | 7/1995 | Berthier | |
| 5,681,283 A | 10/1997 | Brownfield | |
| 5,694,978 A * | 12/1997 | Heilmann | A61M 39/20 138/103 |
| 5,792,120 A | 8/1998 | Menyhay | |
| 5,885,249 A | 3/1999 | Irisawa | |
| 6,045,539 A | 4/2000 | Menyhay | |
| 6,171,287 B1 | 1/2001 | Lynn et al. | |
| 6,322,540 B1 | 11/2001 | Grabis et al. | |
| 6,391,003 B1 | 5/2002 | Lesch, Jr. | |
| 6,409,706 B1 | 6/2002 | Loy | |
| 6,547,764 B2 | 4/2003 | Larsen et al. | |

(Continued)

FOREIGN PATENT DOCUMENTS

| EP | 0409180 A1 | 1/1991 |
|---|---|---|
| EP | 0520930 A1 | 12/1992 |

(Continued)

*Primary Examiner* — Lauren P Farrar
(74) *Attorney, Agent, or Firm* — Cantor Colburn LLP

(57) ABSTRACT

A capping device for disinfecting an access portion of a medical implement is provided. The device includes a housing for covering the access portion of the medical implement having an opening and a cavity having a surface, a disinfecting pad disposed within the cavity and attached to the surface thereof to disinfect the access portion of the medical implement by bringing the disinfecting pad in contact with the access portion of the medical implement, and a resilient member connecting the housing to the medical implement.

19 Claims, 2 Drawing Sheets

(56) References Cited

U.S. PATENT DOCUMENTS

| | | |
|---|---|---|
| 6,582,408 B1 | 6/2003 | Buch-Rasmussen et al. |
| 6,908,460 B2 | 6/2005 | Distefano |
| 7,682,561 B2 | 3/2010 | Davis et al. |
| 7,815,611 B2 | 10/2010 | Giambattista et al. |
| 7,931,877 B2 | 4/2011 | Steffens et al. |
| 8,065,773 B2 | 11/2011 | Vaillancourt et al. |
| 8,069,523 B2 | 12/2011 | Vaillancourt et al. |
| 8,172,825 B2 | 5/2012 | Solomon et al. |
| 8,177,761 B2 | 5/2012 | Howlett et al. |
| 8,197,749 B2 | 6/2012 | Howlett et al. |
| 8,231,587 B2 | 7/2012 | Solomon et al. |
| 8,298,196 B1 | 10/2012 | Mansour |
| 8,328,767 B2 | 12/2012 | Solomon et al. |
| 8,336,151 B2 | 12/2012 | Kerr et al. |
| 8,336,152 B2 | 12/2012 | Vaillancourt et al. |
| 8,343,112 B2 | 1/2013 | Solomon et al. |
| 8,491,546 B2 | 7/2013 | Hoang et al. |
| 8,523,830 B2 | 9/2013 | Solomon et al. |
| 8,523,831 B2 | 9/2013 | Solomon et al. |
| 8,641,681 B2 | 2/2014 | Solomon et al. |
| 8,647,308 B2 | 2/2014 | Solomon et al. |
| 8,647,326 B2 | 2/2014 | Solomon et al. |
| 8,671,496 B2 | 3/2014 | Vaillancourt et al. |
| 8,696,820 B2 | 4/2014 | Vaillancourt et al. |
| 8,734,384 B2 | 5/2014 | Boyd et al. |
| 8,740,864 B2 | 6/2014 | Hoang et al. |
| 8,784,388 B2 | 7/2014 | Charles et al. |
| 8,961,475 B2 | 2/2015 | Solomon et al. |
| 8,999,073 B2 | 4/2015 | Rogers et al. |
| 9,039,989 B2 | 5/2015 | Liu et al. |
| 9,079,692 B2 | 7/2015 | Solomon et al. |
| 9,114,915 B2 | 8/2015 | Solomon et al. |
| 9,186,707 B2 | 11/2015 | Vaillancourt et al. |
| 9,192,449 B2 | 11/2015 | Kerr et al. |
| 9,259,284 B2 | 2/2016 | Rogers et al. |
| 9,283,367 B2 | 3/2016 | Hoang et al. |
| 9,283,368 B2 | 3/2016 | Hoang et al. |
| 9,283,369 B2 | 3/2016 | Ma et al. |
| 2008/0095680 A1* | 4/2008 | Steffens ............... A61L 2/18 422/300 |
| 2008/0177250 A1 | 7/2008 | Howlett et al. |
| 2009/0099529 A1* | 4/2009 | Anderson ......... A61M 5/31511 604/192 |
| 2009/0137969 A1 | 5/2009 | Colantonio et al. |
| 2009/0307449 A1 | 12/2009 | Prahlad et al. |
| 2010/0000040 A1* | 1/2010 | Shaw ................... A61M 39/16 15/244.1 |
| 2010/0200017 A1* | 8/2010 | Kerr .................... A61B 1/122 134/6 |
| 2010/0272379 A1 | 10/2010 | Hu et al. |
| 2011/0054440 A1* | 3/2011 | Lewis .................. A61M 39/16 604/506 |
| 2011/0265825 A1* | 11/2011 | Rogers ................. A61M 39/20 134/22.1 |
| 2012/0016318 A1* | 1/2012 | Hoang ................. A61M 39/16 604/288.01 |
| 2012/0302970 A1 | 11/2012 | Tennican |
| 2013/0171030 A1 | 7/2013 | Ferlic et al. |
| 2015/0360021 A1 | 12/2015 | Limdico et al. |
| 2017/0232121 A1 | 8/2017 | Chiu et al. |
| 2018/0064604 A1 | 3/2018 | Drmanovic |
| 2018/0085568 A1 | 3/2018 | Drmanovic |

FOREIGN PATENT DOCUMENTS

| | | |
|---|---|---|
| EP | 0832661 A2 | 4/1998 |
| EP | 1336419 A1 | 8/2003 |
| WO | 2015120336 A1 | 8/2015 |

* cited by examiner

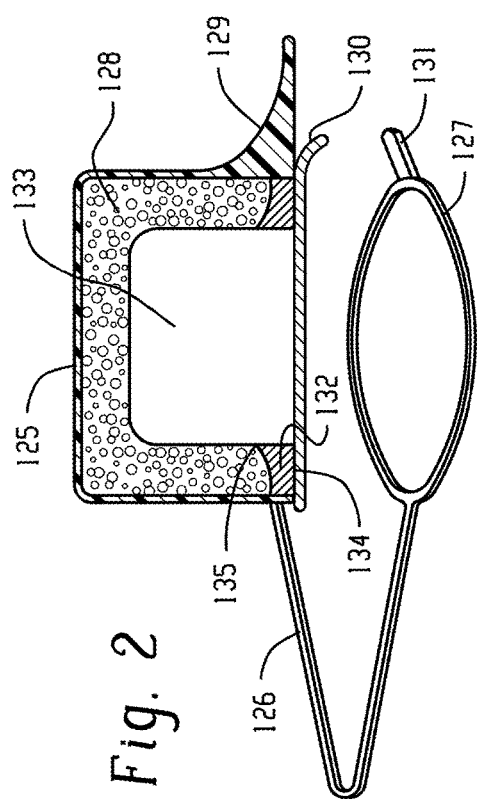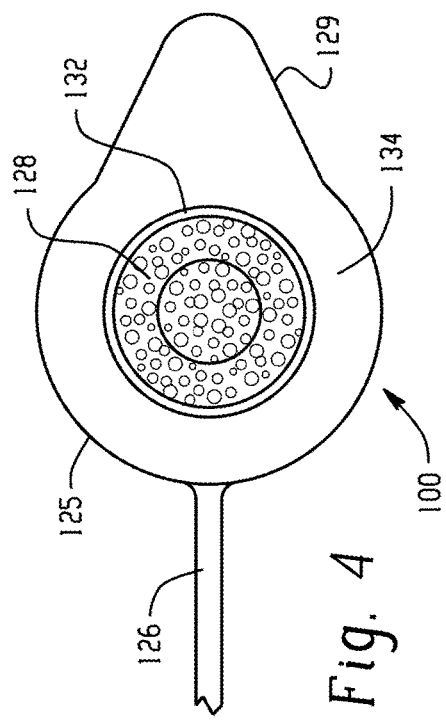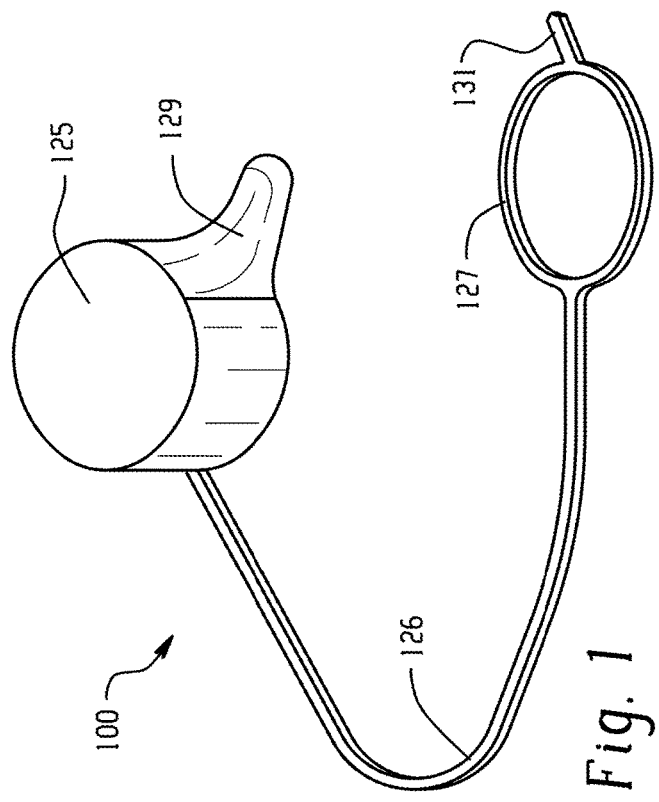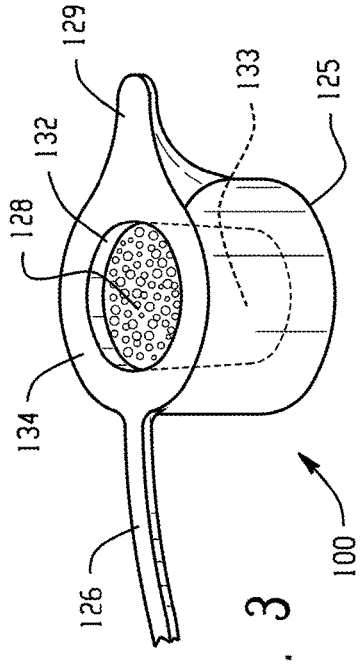

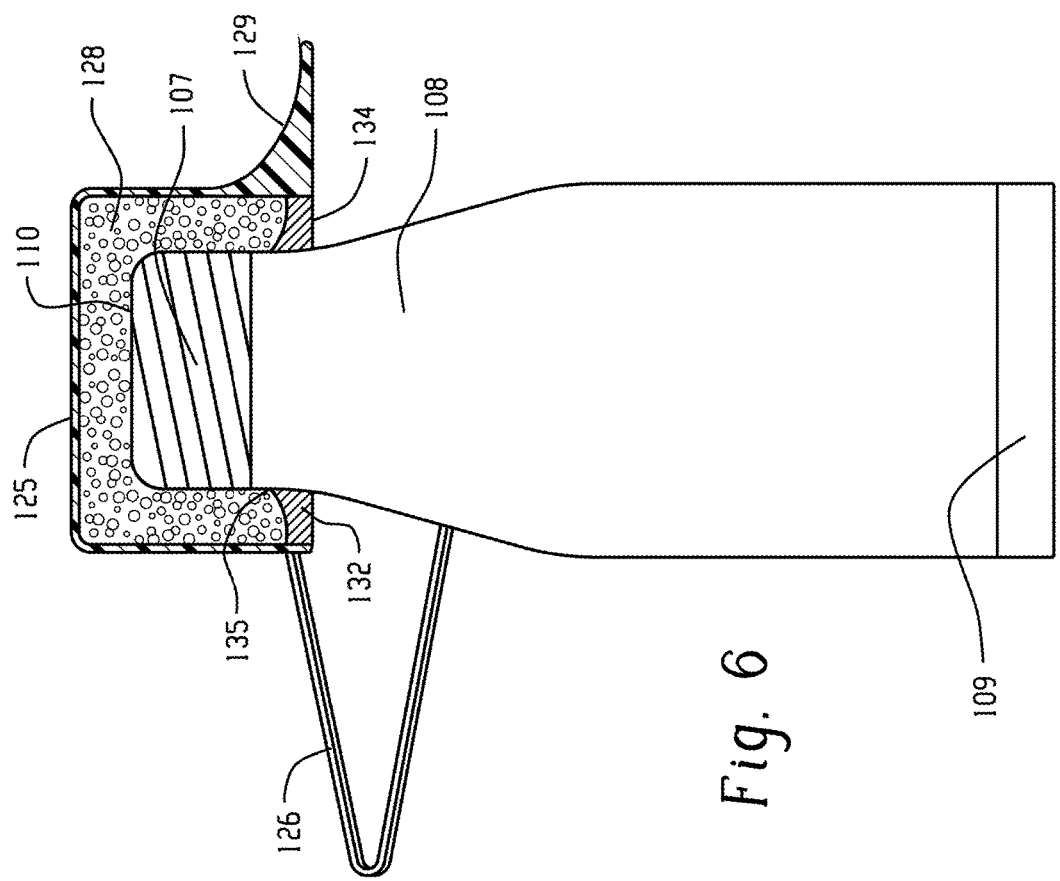
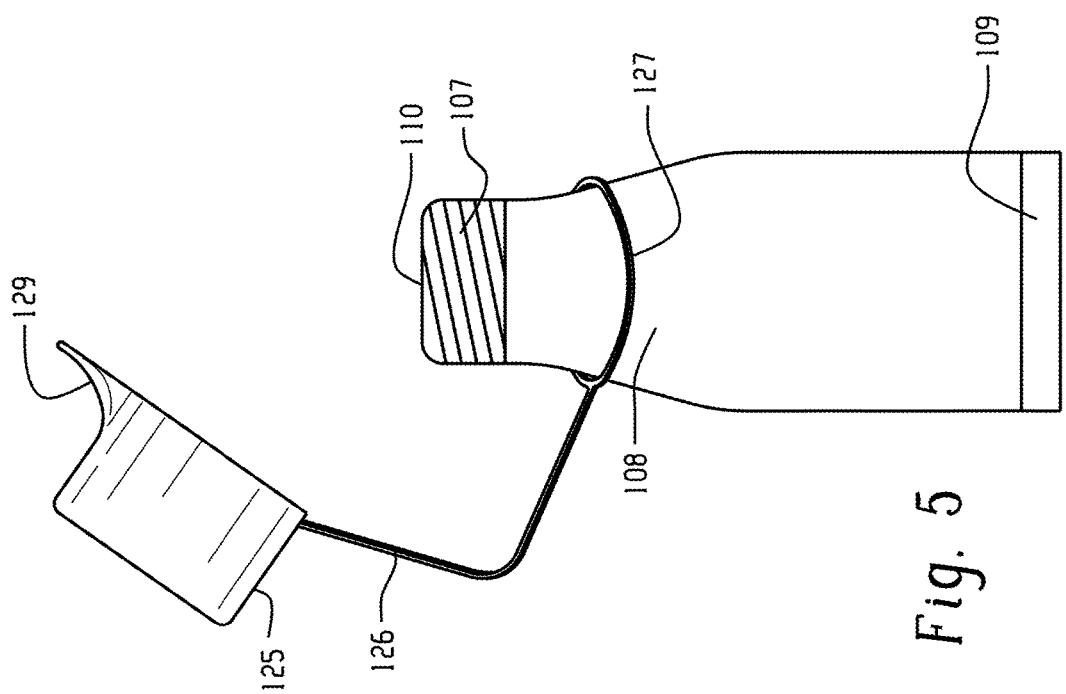

DISINFECTING CAP

BACKGROUND

The present invention generally relates to a device having disinfecting properties, and more specifically, to a capping device for disinfecting a hub or injection port.

Presence of intravenous catheters is the major risk factor for the development of bloodstream infections. These catheters can be either central or peripheral. Needleless hub connectors are ordinarily used as an injection port on the catheters. A typical connector includes a female luer lock, and usually, a syringe with a male luer lock is used to inject fluids or medications.

Needleless hub connector contamination is a major risk factor for bloodstream infection. Scrubbing the female luer lock with alcohol for 10-60 seconds is recommended before each use, but this procedure is often omitted by medical professionals. Studies have shown better results in reducing infection with different types of alcohol impregnated protectors, such as Swab Cap®. However, because the protector constitutes a separate entity, only the most diligent medical professionals would utilize them after every step. In addition, the cap does not assure mandatory compliance. Caps do not always engage the threads on the hub, and the threads can serve as a source of infection, especially, if a dirty or bloody male luer from the syringe is used to engage the hub. Also, because of their small size, the caps are easily contaminated after use if they are placed on a contaminated surface.

Attempts have been made to cover the hub in order to keep it disinfected. However, these efforts either failed to cover the hub completely by shielding only the top membrane, or were too difficult to remove when the port needed to be injected quickly and conveniently.

Thus, there remains a need for a convenient and reliable disinfecting device that would guarantee 100% compliance of medical professionals with antiseptic techniques.

SUMMARY

In an embodiment, a capping device for disinfecting an access portion of a medical implement is provided. The device includes a housing for covering the access portion of the medical implement having an opening and a cavity having a surface, a disinfecting pad disposed within the cavity and attached to the surface thereof to disinfect the access portion of the medical implement by bringing the disinfecting pad in contact with the access portion of the medical implement, and a resilient member connecting the housing to the medical implement.

The disinfecting pad may be disposed over the entire surface of the cavity. When the disinfecting pad is in contact with the access portion of the medical device, the disinfecting pad may release the disinfecting agent onto the access portion of the medical device to disinfect the access portion of the medical device.

The device may further include a hollow disposed between the disinfecting pad and the opening of the housing, wherein the shape of the hollow substantially matches the shape of the access portion of the medical implement.

The device may further include a sealing member disposed between the housing and the medical implement to provide a tight connection therebetween and to prevent or minimize loss of the disinfecting agent.

The device may further include a protecting member to prevent loss of the disinfecting agent when the housing is disconnected from the medical implement.

The resilient member may include a loop disposed around the medical implement and a connector attached to the housing. An adhesive material may be disposed between the loop and the medical implement to affix the loop to the medical implement. The connector may include an elastic material.

The device may further include a handle attached to the housing. The handle may be located at a point substantially opposite to the point of attachment of the resilient member to the housing.

The housing may not include threading protruded inwardly inside the cavity near the opening.

The housing may include a polyalkylene material, a polyester material, a polyurethane material, a silicone material, a cotton material, or a combination thereof.

The disinfecting pad may include a sponge. The disinfecting agent may include an antibacterial agent, an antiviral agent, or a combination thereof.

In another embodiment, a method for disinfecting an access portion of a medical implement is provided. The method includes providing a capping device having a housing for covering the access portion of the medical implement, wherein the housing comprises an opening and a cavity having a surface, a disinfecting pad disposed within the cavity and attached to the surface thereof to disinfect the access portion of the medical implement by bringing the disinfecting pad in contact with the access portion of the medical implement, and a resilient member connecting the housing to the medical implement. The method further includes attaching the device to the access portion of the medical implement.

The method may further include detaching the device from the access portion of the medical implement prior to injection of a fluid into the medical implement.

The resilient member may include a loop disposed around the medical implement and a connector attached to the housing.

The disinfecting pad may be disposed over the entire surface of the cavity.

BRIEF DESCRIPTION OF THE DRAWINGS

The above and other aspects and features of the present disclosure will become more apparent by describing in detail exemplary embodiments thereof with reference to the attached drawings, in which:

FIG. 1 is a view of an embodiment of the capping device completely detached from a medical implement;

FIG. 2 is cross-sectional view of an embodiment of the capping device completely detached from a medical implement;

FIG. 3 is a perspective view of an embodiment of the capping device completely detached from the access portion of the medical implement;

FIG. 4 is an end elevation view of an embodiment of the capping device showing a disinfecting pad lining and a rubber sealing ring;

FIG. 5 is a side view of an embodiment of the capping device attached to the medical implement with a housing displaced from the access portion of the medical implement; and FIG. 6 is a cross-sectional view of an embodiment of the capping device with the hollow covering the access portion of the medical implement and its side threads.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below by referring to the figures to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third, etc., may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross-section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"Substantially" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "substantially" can mean within one or more standard deviations, or within ±30%, 20%, 10%, 5% of the stated value.

In an embodiment, a capping device for disinfecting an access portion of a medical implement is provided. The device includes a housing for covering the access portion of the medical implement having an opening and a cavity having a surface, a disinfecting pad disposed within the cavity and attached to the surface thereof to disinfect the access portion of the medical implement by bringing the disinfecting pad in contact with the access portion of the medical implement, and a resilient member connecting the housing to the medical implement.

Referring to FIG. 1, the capping device 100 includes a housing 125 and a resilient member attached to the housing 125. The housing 125 includes an opening and a cavity comprising a surface. The resilient member includes a connector 126, which may be an elastic band, and a loop 127. The housing may have a handle 129 attached to it. The point of attachment of the handle 129 to the housing 125 may be substantially opposite to the point of attachment of the connector 126 to the housing 125. The housing may include a polyalkylene material (such as polyethylene or polypropylene), a polyester material, a polyurethane material, a silicone material, a cotton material, or a combination thereof.

FIG. 2 is a cross-sectional view of an embodiment of the capping device 100. The housing 125 protrudes laterally into the handle 129, which provides an additional gripping surface and is important for removing the housing 125 from the access portion of the medical implement (such as a hub) and for placing it onto the access portion of the medical implement. The handle may have some gripping features like ridges or grooves to help coupling and decoupling it from the implement. Located inside the housing 125 is a disinfecting pad 128 impregnated with a disinfecting agent. The disinfecting pad 128 lines the interior of the housing 125 and is affixed to the surface of the cavity. The disinfecting pad 128 does not completely fill out the entire housing 125. It leaves an empty space, which is a hollow 133 (or a central accepting chamber), which matches the size and the shape of the access portion of the medical implement. This compatibility guarantees that the disinfecting pad 128 comes into close contact with the injection membrane and female luer threads of the medical implement. The disinfecting pad 128 may have great absorption capacity, and pressure applied to push the housing 125 down to cover the access portion of the medical implement may cause compression of the disinfecting pad 128 and release of the disinfecting agent onto the injection membrane 110 and around the female luer threads 107. Movement of the medical implement also causes the disinfecting agent to migrate inside the housing 125 to disinfect the access portion of the implement. The disinfecting pad may include a sponge. The disinfecting agent may include an antibacterial agent, an antiviral agent, or a combination thereof.

Located at the bottom of the housing 125 is the housing floor 134, and located above it is a sealing member 132, which provides a good seal with the access portion of the medical implement to minimize loss of the disinfecting agent. The central rim 135 of the sealing member 132 is elevated and serves to minimize the loss of the disinfecting agent when the housing 125 is disconnected from the medical implement because the liquid disinfecting agent flows toward the periphery of the housing 125. At the bottom of the cap is a protecting device 130, which may be a peelable foil. The protecting device 130 prevents loss of the disinfecting agent and drying of the disinfecting pad 128 before the capping device 100 is used for the first time.

The housing 125 is connected to the loop 127 by a connector 126 (such as an elastic band), which is flexible enough to allow the housing 125 to come down and cover the access portion of the medical implement. The connector 126 may be biased to keep the housing 125 above but in close proximity to the access portion of the medical implement when the injection membrane 110 of the implement is accessed for injection of fluids (for example, medication). The loop 127 has a diameter similar to the diameter of the neck of the most common medical implements (such as hubs). Its inner surface may be covered with an adhesive material which is revealed after a safety tape 131 is removed. This adhesive material may help provide a better connection between the loop 127 and the neck 108 of the medical implement. However, this may not be necessary because the shape and size of the loop 127 fits the neck of the implement 108 well enough, so the perfect connection may not be absolutely necessary since it is important for the housing 125 just to be close to the access portion of the medical implement when the implement is in use.

FIG. 3 is an enlarged perspective view of the housing 125 with the housing floor 134, the handle 129 and a part of the connector 126. The sealing member 132 and its central elevated rim 135 may be partially seen. The disinfecting pad 128 may only partially be seen because the housing floor 134 almost completely covers the disinfecting pad 128. The shape and size of the disinfecting pad 128 and the central accepting chamber 133 (the hollow) is shown with a dotted line.

FIG. 4 is a bottom view of the capping device 100 which shows the housing floor 134 which covers only the periphery of the housing 125. The housing floor 134 extends into the handle 129, which helps apply the capping device 100 onto the top of the medical implement and remove the cap 125 from the neck of the implement 108. Opposite to the handle 129 is the connector 126. FIGS. 2 and 6 also partially show the sealing member 132, and its central part, which is the central rim 135. This view also shows the shape of the disinfecting pad 128 and the central accepting chamber 133 (the hollow) shown here as an empty space ready to accept the access portion of the implement.

FIG. 5 is a side view of an embodiment of the capping device 100 with the housing 125 displaced from the access portion of the medical implement so that the injection membrane 110 and the female luer threads 107 may be exposed and ready to connect with a syringe for medication injection or drawing of fluids. The connector 126 may be flexible so the housing 125 may be pushed further away to allow easy access to the medical implement. The connector 126 may be biased to come in close proximity to the medical implement once the injection has been completed so that it would remind a medical professional to push it down after each use and cover the access portion of the implement. This view also shows the loop 127 which is placed around the neck of the implement 108, thus preventing separation of the capping device 100 from the medical implement. This is an important feature of the capping device 100 because all other products on the market like Swab Cap® are completely disconnected during medical implement use, and very often placed on a non-sterile surface and either lost or forgotten about. Visualization of the housing 125 and close proximity to the medical implement does not guarantee total compliance but significantly improves the chances that a medical professional would apply the capping device 100 to the access portion of the medical implement and would keep it covered and in contact with the disinfecting agent. In contrast, most protective caps on the market have male luer threads and need a rotating move for the cap and the hub to connect. In the capping device 100, according to an embodiment, it is not necessary for housing 125 to have threads since it should attach and hold well when a provider merely places it onto the access portion of the medical implement.

FIG. 6 is a cross-sectional view of an embodiment of the capping device 100. The housing 125 may be seen covering the access portion of the medical implement with the disinfecting pad 128 contacting the injection membrane 110 and the female luer threads 107 of the medical implement. The handle 129 and the sealing member 132 with the raised central rim 135 may also be seen in this figure. Located substantially opposite to the handle 129 is the connector 126, which keeps the medical implement and the housing 125 together. The diameter of the opening on the bottom of the cap matches well with the diameter of the access portion of the medical implement to provide a slip lock connection which also helps to keep the housing 125 and the implement together. The sealing member 132 not only provides a good seal to prevent loss of the disinfecting agent but also helps to keep the capping device 100 and the medical implement together.

In another embodiment, a method for disinfecting an access portion of a medical implement is provided. The method includes providing a capping device having a housing for covering the access portion of the medical implement, wherein the housing comprises an opening and a cavity having a surface, a disinfecting pad disposed within the cavity and attached to the surface thereof to disinfect the access portion of the medical implement by bringing the disinfecting pad in contact with the access portion of the medical implement, and a resilient member connecting the housing to the medical implement. The method further includes attaching the device to the access portion of the medical implement.

The method may further include detaching the device from the access portion of the medical implement prior to injection of a fluid into the medical implement.

The capping device, according to an embodiment, is a fairly simple and affordable way to bring compliance of medical practitioners to an essentially complete level. It would take a very irresponsible healthcare provider to intentionally not close the access portion of the medical implement. Most of the known hub protective caps have a male luer lock and require two hands to attach or detach the cap from the hub. Once separated, the cap can be lost or placed on a contaminated surface. The capping device, according to an embodiment, includes a cap loosely attached to the hub, biased toward a position close to the top of the hub, which can be easily removed from the hub with a thumb because of a slip lock design (only one hand is needed to open or close the hub), so that the other hand can be used to hold a syringe for the injection.

The present inventive concept has been described in terms of exemplary principles and embodiments, but those skilled in the art will recognize that variations may be made and equivalents substituted for what is described without departing from the scope and spirit of the disclosure as defined by the following claims.

What is claimed is:

1. A capping device for disinfecting an access portion of a medical implement, comprising:
    a housing for covering the access portion of the medical implement, wherein the access portion comprises an injection membrane and female luer threads, and wherein the housing comprises an opening, a cavity comprising a continuous inner surface facing the opening, and a housing floor extending inside the cavity of the housing,
    a disinfecting pad disposed within the cavity and attached to the inner surface thereof to disinfect the injection membrane and female luer threads of the medical implement by bringing the disinfecting pad in a direct and prolonged contact with the injection membrane and female luer threads,
    a sealing member disposed between the housing and the medical implement to provide a non-permanent tight connection therebetween, wherein the sealing member extends inside the cavity of the housing and is disposed between the housing floor and the disinfecting pad, wherein the sealing member comprises a central rim proximal to the medical implement, and wherein the central rim is elevated towards the inner surface of the housing to prevent loss of the disinfecting agent, and
    a resilient member connecting the housing to the medical implement.

2. The device according to claim 1, wherein the disinfecting pad is impregnated with a disinfecting agent prior to attachment of the housing to the access portion of the medical implement.

3. The device according to claim 1, wherein the disinfecting pad is disposed over and in contact with the entire inner surface of the cavity.

4. The device according to claim 1, further comprising a hollow disposed between the disinfecting pad and the opening of the housing, wherein the shape of the hollow substantially matches the shape of the injection membrane and female luer threads of the medical implement.

5. The device according to claim 1, wherein when the disinfecting pad is in contact with the injection membrane and female luer threads of the medical implement, the disinfecting pad releases the disinfecting agent onto the injection membrane and female luer threads of the medical implement to disinfect the injection membrane and female luer threads.

6. The device according to claim 1, further comprising a protecting member to prevent loss of the disinfecting agent when the housing is disconnected from the medical implement.

7. The device according to claim 1, wherein the resilient member comprises a loose flexible loop disposed around the medical implement and separately from the female luer threads thereof, and a flexible connector connecting the housing and the loose flexible loop.

8. The device according to claim 7, further comprising an adhesive material disposed between the loop and the medical implement to affix the loop to the medical implement.

9. The device according to claim 7, wherein the connector comprises an elastic material.

10. The device according to claim 1, further comprising a handle attached to the housing.

11. The device according to claim 10, wherein the handle is located at a point substantially opposite to the point of attachment of the resilient member to the housing across the opening of the housing.

12. The device according to claim 1, wherein the housing does not comprise threading protruded inwardly inside the cavity near the opening.

13. The device according to claim 1, wherein the disinfecting pad comprises a sponge.

14. The device according to claim 1, wherein the housing comprises a polyalkylene material, a polyester material, a polyurethane material, a silicone material, a cotton material, or a combination thereof.

15. The device according to claim 1, wherein the disinfecting agent comprises an antibacterial agent, an antiviral agent, or a combination thereof.

16. A method for disinfecting an access portion of a medical implement, comprising:
    providing a capping device comprising:
        a housing for covering the access portion of the medical implement, wherein the access portion comprises an injection membrane and female luer threads, and wherein the housing comprises an opening, a cavity comprising a continuous inner surface facing the opening, and a housing floor extending inside the cavity of the housing,
        a disinfecting pad disposed within the cavity and attached to the inner surface thereof to disinfect the injection membrane and female luer threads of the medical implement by bringing the disinfecting pad in direct and prolonged contact with the injection membrane and female luer threads,
        a sealing member disposed between the housing and the medical implement to provide a non-permanent tight connection therebetween, wherein the sealing member extends inside the cavity of the housing and is disposed between the housing floor and the disinfecting pad, wherein the sealing member comprises a central rim proximal to the medical implement, and wherein the central rim is elevated towards the inner surface of the housing to prevent or minimize loss of the disinfecting agent, and
        a resilient member connecting the housing to the medical implement, and
    attaching the device to the access portion of the medical implement.

17. The method according to claim 16, further comprising:
    detaching the device from the access portion of the medical implement prior to injection of a fluid into the medical implement.

18. The method according to claim 16, wherein the resilient member comprises a loose flexible loop disposed around the medical implement and separately from the female luer threads thereof, and a flexible connector connecting the housing and the loose flexible loop.

19. The method according to claim 16, wherein the disinfecting pad is disposed over and in contact with the entire inner surface of the cavity.

* * * * *